(12) United States Patent
Cai et al.

(10) Patent No.: US 12,054,482 B2
(45) Date of Patent: Aug. 6, 2024

(54) TLR8 AGONIST

(71) Applicant: CHIA TAI TIANQING PHARMACEUTICAL GROUP CO., LTD., Jiangsu (CN)

(72) Inventors: Zhe Cai, Shanghai (CN); Fei Sun, Shanghai (CN); Charles Z. Ding, Shanghai (CN); Shuhui Chen, Shanghai (CN)

(73) Assignee: CHIA TAI TIANQING PHARMACEUTICAL GROUP CO., LTD., Lianyungang (CN)

(*) Notice: Subject to any disclaimer, the term of this patent is extended or adjusted under 35 U.S.C. 154(b) by 719 days.

(21) Appl. No.: 17/276,920

(22) PCT Filed: Sep. 19, 2019

(86) PCT No.: PCT/CN2019/106687
§ 371 (c)(1),
(2) Date: Mar. 17, 2021

(87) PCT Pub. No.: WO2020/057604
PCT Pub. Date: Mar. 26, 2020

(65) Prior Publication Data
US 2021/0371414 A1 Dec. 2, 2021

(30) Foreign Application Priority Data
Sep. 19, 2018 (CN) .......................... 201811094969.4

(51) Int. Cl.
C07D 471/04 (2006.01)
A61K 31/549 (2006.01)
A61P 37/02 (2006.01)

(52) U.S. Cl.
CPC .......... C07D 471/04 (2013.01); A61K 31/549 (2013.01); A61P 37/02 (2018.01)

(58) Field of Classification Search
CPC ........ C07D 471/04; A61P 37/02; A61P 31/12; A61P 31/20; A61K 31/519; A61K 31/549
See application file for complete search history.

(56) References Cited

U.S. PATENT DOCUMENTS

| | | | |
|---|---|---|---|
| 8,895,577 B2 | 11/2014 | Wu et al. | |
| 8,916,575 B2 | 12/2014 | McGowan et al. | |
| 9,670,205 B2 | 6/2017 | Aktoudianakis et al. | |
| 2008/0312227 A1 | 12/2008 | De Jonghe et al. | |
| 2014/0073642 A1 | 3/2014 | McGowan et al. | |
| 2018/0086755 A1 | 3/2018 | Chin et al. | |
| 2021/0371414 A1 | 12/2021 | Cai et al. | |

FOREIGN PATENT DOCUMENTS

| | | | |
|---|---|---|---|
| CN | 102015651 A | 8/2011 | |
| CN | 103748081 | 4/2014 | |
| CN | 103748081 A | 4/2014 | |
| CN | 107108615 A | 8/2017 | |
| EA | 018068 | 5/2013 | |
| EA | 028254 | 10/2017 | |
| EP | 3854794 | 7/2021 | |
| JP | 2011513413 | 4/2011 | |
| JP | 2014516958 | 7/2014 | |
| JP | 2017509667 | 4/2017 | |
| RU | 2007135053 | 3/2009 | |
| WO | WO 2013022766 | 2/2013 | |
| WO | WO 2014076221 | 5/2014 | |
| WO | WO 2016141092 | 9/2016 | |
| WO | WO-2016141092 A1 * | 9/2016 | ........... A61K 31/517 |
| WO | 2018045150 A1 | 3/2018 | |
| WO | WO 2018045144 | 3/2018 | |
| WO | WO 2020057604 | 3/2020 | |

OTHER PUBLICATIONS

International Search Report for PCT/CN2019/106687, mailed Dec. 18, 2019. 5 pages.
Extended European Search Report in European Appln. No. 19862693.9, dated May 17, 2022, 7 pages.
Office Action in Chinese Appln. No. 201980052513.8, dated Feb. 8, 2022, 10 pages (with English translation).
Suárez et al., "Inhibitors of the TAM subfamily of tyrosine kinases: Synthesis and biological evaluation," European Journal of Medicinal Chemistry, Mar. 2013, 61:2-25.
Traoré et al., "New aminopyrimidine derivatives as inhibitors of the TAM family," European Journal of Medicinal Chemistry, Dec. 2013, 70:789-801.

* cited by examiner

*Primary Examiner* — Robert H Havlin
*Assistant Examiner* — Chantal Adlam
(74) *Attorney, Agent, or Firm* — Fish & Richardson P.C.

(57) ABSTRACT

A TLR8 (Toll-like receptor 8) agonist, a compound of the structure shown in formula (I), an isomer thereof, or a pharmaceutically acceptable salt thereof.

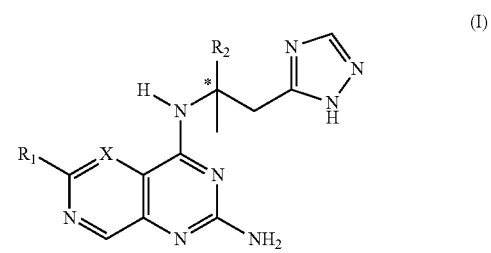

11 Claims, No Drawings

TLR8 AGONIST

CROSS-REFERENCE TO RELATED APPLICATIONS

The present application is a U.S. National Phase application under 35 U.S.C. § 371 of International Patent Application No. PCT/CN2019/106687, filed on Sep. 19, 2019, which claims the benefit and priority of the Chinese Patent Application No. 201811094969.4, filed with the National Intellectual Property Administration, PRC on Sep. 19, 2018, the content of which is incorporated herein by reference in its entirety.

TECHNICAL FIELD

The present application relates to a novel toll-like receptor 8 (TLR8) agonist, and in particular relates to: a compound of formula (I), an isomer thereof or a pharmaceutically acceptable salt thereof; a pharmaceutical composition comprising the compound or the pharmaceutically acceptable salt thereof; and use of the compound of formula (I) or the pharmaceutically acceptable salt thereof and the pharmaceutical composition in treating or preventing a disease responsive to TLR8 agonism.

BACKGROUND

Toll-like receptors (TLRs) are an important class of protein molecules involved in non-specific immunity (innate immunity), and are also a bridge linking non-specific immunity and specific immunity. TLRs are single transmembrane non-catalytic proteins that are expressed primarily in a range of immune cells such as dendritic cells, macrophages, monocytes, T cells, B cells, and NK cells. TLRs are capable of recognizing molecules with conserved structures derived from microorganisms. They can recognize the microorganisms and activate the body to generate immune cell responses when microorganisms break through the physical barriers of the body, such as skin and mucosa. For example, TLR1, TLR2, TLR4, TLR5 and TLR6 mainly recognize extracellular stimuli such as lipopolysaccharide, lipopeptide, and flagellin of bacteria, while TLR3, TLR7, TLR8 and TLR9 function in cell endosomes, such as binding to their ligands after phagocytosis and dissolution of the envelope and recognizing nucleic acids of microorganisms.

Among the different subtypes of TLR, TLR8 has unique functions: TLR8 is expressed primarily in monocytes, macrophages, and myeloid dendritic cells. The signaling pathway of TLR8 can be activated by bacterial single-stranded RNAs, small molecule agonists, and microRNAs. Activation of TLR8 results in the production of Th1 polar cytokines such as IL-12, IL-18, TNF-α and IFN-γ, and various co-stimulatory factors such as CD80 and CD86. These cytokines can activate and amplify innate and adaptive immune responses and provide a beneficial treatment regimen for diseases involving anti-virus, anti-infection, autoimmunity, tumors, and the like. For example, with respect to hepatitis B, activation of TLR8 on antigen presenting cells and other immune cells in the liver can activate cytokines such as IL-12, which in turn activates specific T cells and NK cells that are depleted by the virus, thereby reconstituting the antiviral immunity in the liver.

The selective TLR8 agonist VTX-2337 from VentiRX Pharmaceuticals is first used clinically for the evaluation of different tumors, and the mode of administration of VTX-2337 is subcutaneous injection. Gilead Sciences reported an oral TLR8 agonist for the treatment of chronic hepatitis B infection, which is currently in clinical phase II. However, its structure has not disclosed yet.

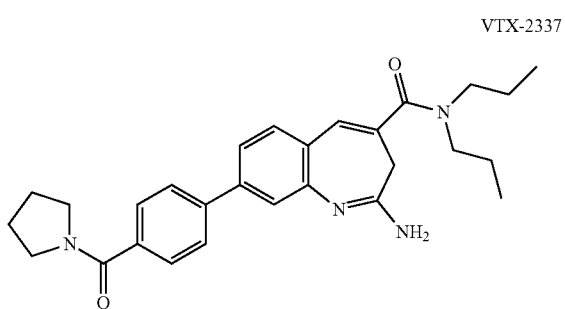 [SMILES: CCCN(CCC)C(=O)C1=Cc2ccc(-c3ccc(C(=O)N4CCCC4)cc3)cc2N=C(N)C1]

VTX-2337

A series of TLR8 agonists were reported in patent WO2016141092 of Gilead Sciences, such as formula 1 with an $AC_{50}$ of 0.02 μM in agonizing TLR8 to induce the production of specific cytokine IL-12p40 (data cited from Table 1 of WO2016141092), wherein $AC_{50}$ represents the concentration of compound corresponding to half maximal agonistic effect. In patent WO2016141092, compounds containing five-membered nitrogen heterocycles were reported as well, such as formula 2 and formula 3. However, formula 2 and formula 3 have poor activity in agonizing TLR8 to induce the production of specific cytokine IL-12p40, with $AC_{50}$ being 21.5 μM and 3.4 μM respectively (data cited from Table 1 of WO2016141092). Formula 1, formula 2 and formula 3 are Examples 61, 55 and 56 disclosed in WO2016141092 respectively.

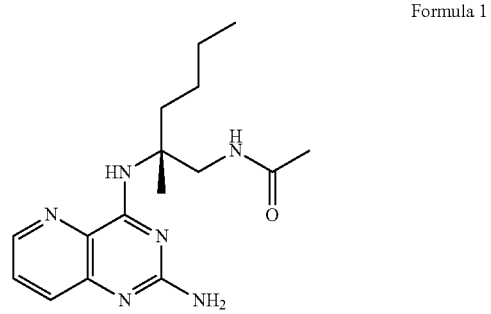

Formula 1

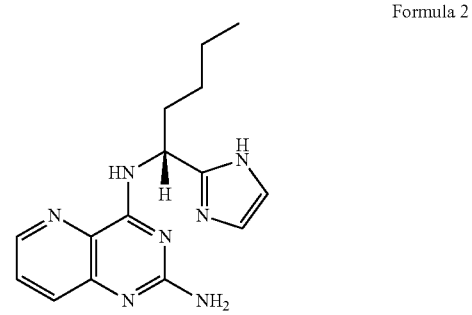

Formula 2

-continued

Formula 3

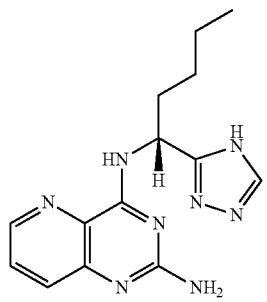

SUMMARY OF THE INVENTION

The present application provides a compound of formula (I), an isomer thereof or a pharmaceutically acceptable salt thereof,

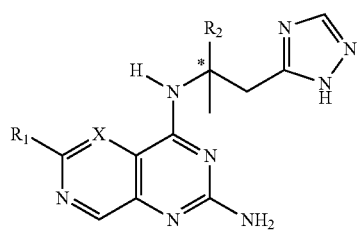

(I)

wherein, the carbon atom with "*" may be a chiral carbon atom present in a form of a single (R) or (S) enantiomer or in a form enriched with one enantiomer;

X is selected from the group consisting of N and CH;

$R_1$ is selected from the group consisting of H, F, Cl, Br, I, CN, $C_{1-6}$ alkyl, $C_{3-6}$ cycloalkyl, —N($R_a$)($R_b$) and —O($R_c$), the $C_{1-6}$ alkyl and $C_{3-6}$ cycloalkyl being optionally substituted with 1, 2 or 3 $R_d$;

$R_2$ is $C_{1-6}$ alkyl, the $C_{1-6}$ alkyl being optionally substituted with 1, 2 or 3 $R_e$;

$R_a$, $R_b$, $R_c$, $R_d$ and $R_e$ are each independently selected from the group consisting of H, F, Cl, Br, I, OH, CN, $NH_2$, $CH_3$,

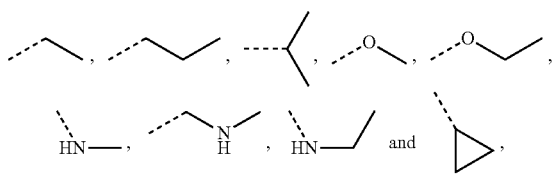

the $CH_3$,

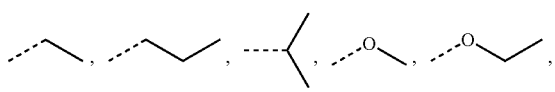

-continued

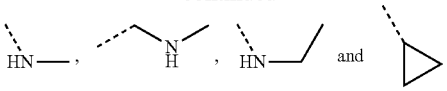

being optionally substituted with 1, 2 or 3 R; and each R is independently selected from the group consisting of F, Cl, Br, I, OH, CN, $NH_2$, $CH_3$, The present application provides a compound of formula (I'), an isomer thereof or a pharmaceutically acceptable salt thereof, (I')

wherein,

X is selected from the group consisting of N and CH;

$R_1$ is selected from the group consisting of H, F, Cl, Br, I, CN, $C_{1-6}$ alkyl, $C_{3-6}$ cycloalkyl, —N($R_a$)($R_b$) and —O($R_c$), the $C_{1-6}$ alkyl and $C_{3-6}$ cycloalkyl being optionally substituted with 1, 2 or 3 $R_d$;

$R_2$ is $C_{1-6}$ alkyl, the $C_{1-6}$ alkyl being optionally substituted with 1, 2 or 3 $R_e$;

$R_a$, $R_b$, $R_c$, $R_d$ and $R_e$ are each independently selected from the group consisting of H, F, Cl, Br, I, OH, CN, $NH_2$, $CH_3$, the CH₃,

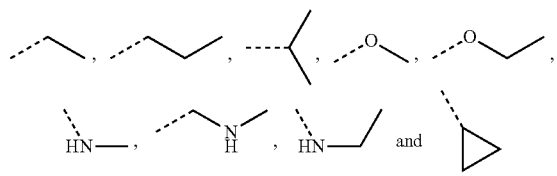

being optionally substituted with 1, 2 or 3 R; and
each R is independently selected from the group consisting of F, Cl, Br, I, OH, CN, NH₂, CH₃,

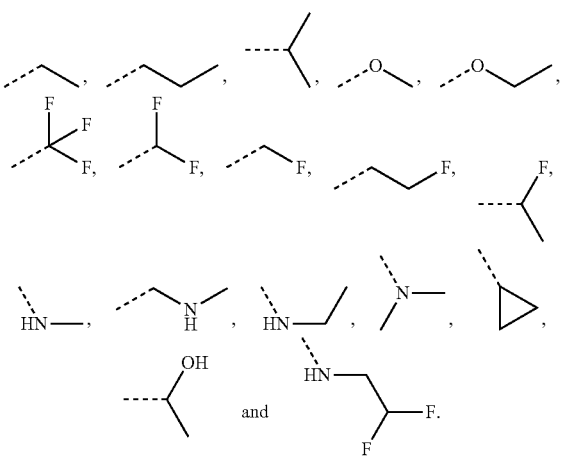

In some embodiments of the present application, R$_a$, R$_b$, R$_c$, R$_d$ and R$_e$ are each independently selected from the group consisting of H, F, Cl, Br, I, OH, CN, NH₂, CH₃,

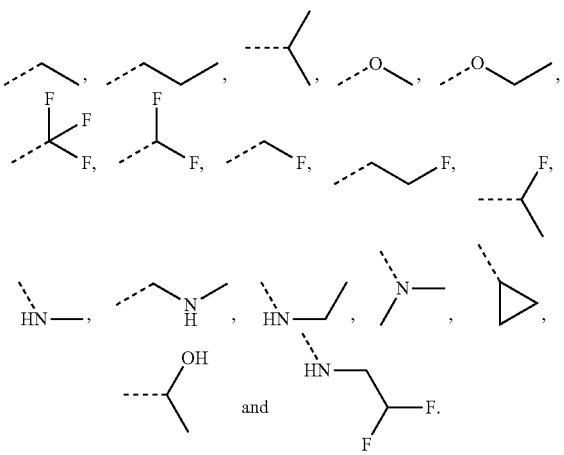

In some embodiments of the present application, R₁ is selected from the group consisting of H, F, Cl, Br, I, CN, CH₃,

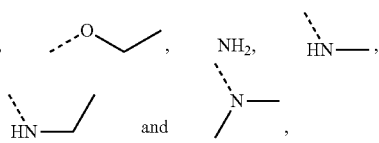

cyclopentyl, cyclobutyl,

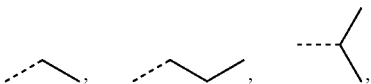

the CH₃,

cyclopentyl and cyclobutyl being optionally substituted with 1, 2 or 3 R$_d$.

In some embodiments of the present application, R₁ is selected from the group consisting of H, F, Cl, Br, I, CH₃ and

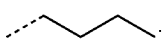

In some embodiments of the present application, R₂ is selected from the group consisting of

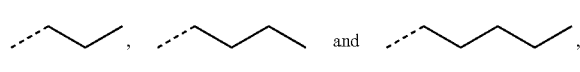

the

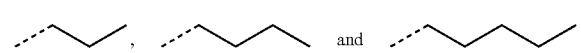

being optionally substituted with 1, 2 or 3 R$_e$.

In some embodiments of the present invention, R₂ is

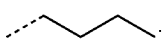

The present application also provides a compound of the formula below, an isomer thereof or a pharmaceutically acceptable salt thereof,

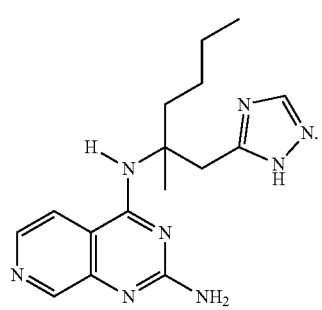

In some embodiments of the present application, provided is the compound, the isomer thereof or the pharmaceutically acceptable salt thereof, selected from

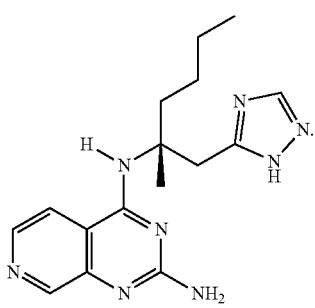

In some embodiments of the present application, $R_a$, $R_b$, $R_c$, $R_d$ and $R_e$ are each independently selected from the group consisting of H, F, Cl, Br, I, OH, CN, $NH_2$, $CH_3$,

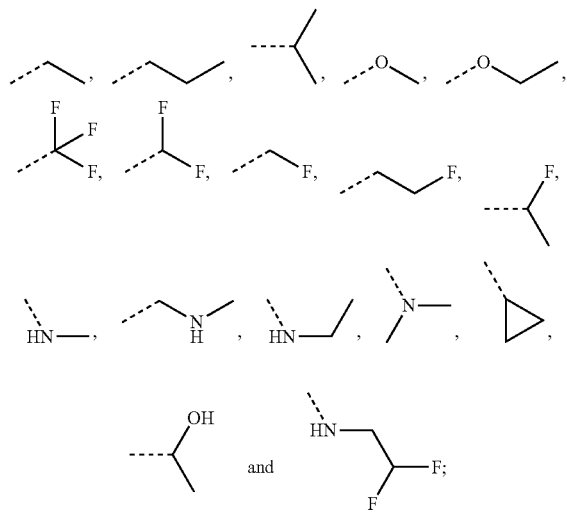

the other variables are defined as above.

In some embodiments of the present application, $R_1$ is selected from the group consisting of H, F, Cl, Br, I, CN, $CH_3$,

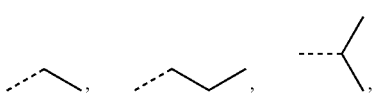

cyclopentyl, cyclobutyl,

$NH_2$,

the $CH_3$,

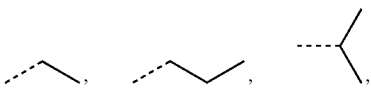

cyclopentyl and cyclobutyl being optionally substituted with 1, 2 or 3 $R_d$.

In some embodiments of the present application, $R_1$ is selected from the group consisting of H, F, Cl, Br, I, $CH_3$ and

the other variables are defined as above.

In some embodiments of the present application, $R_2$ is selected from the group consisting of

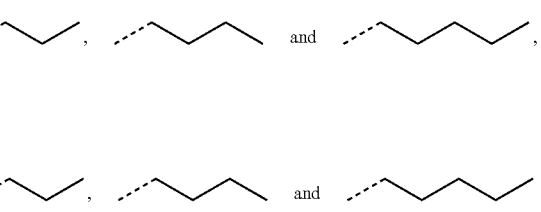

being optionally substituted with 1, 2 or 3 $R_e$; the other variables are defined as above.

In some embodiments of the present invention, $R_2$ is

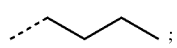

the other variables are defined as above.

Some other embodiments of the present application can be obtained by the arbitrary combination of the above variables.

In another aspect, the present application provides a pharmaceutical composition comprising the compound, the isomer thereof or the pharmaceutically acceptable salt thereof disclosed herein. In some embodiments, the pharmaceutical composition disclosed herein further comprises a pharmaceutically acceptable excipient.

In another aspect, the present application provides a method for agonizing TLR8, comprising administering to a subject in need (preferably a human) a therapeutically effective amount of the compound, the isomer thereof, the pharmaceutically acceptable salt thereof, or the pharmaceutical composition thereof disclosed herein.

In another aspect, the present application provides a method for treating or preventing a disease responsive to TLR8 agonism, comprising administering to a subject in need (preferably a human) a therapeutically effective amount of the compound, the isomer thereof, the pharmaceutically acceptable salt thereof, or the pharmaceutical composition thereof disclosed herein.

In another aspect, the present application provides use of the compound, the isomer thereof, the pharmaceutically acceptable salt thereof, or the pharmaceutical composition thereof disclosed herein in manufacturing a medicament for treating or preventing a disease responsive to TLR8 agonism.

In another aspect, the present application provides use of the compound, the isomer thereof, the pharmaceutically acceptable salt thereof, or the pharmaceutical composition thereof disclosed herein in treating or preventing a disease responsive to TLR8 agonism.

In another aspect, the present application provides the compound, the isomer thereof, the pharmaceutically acceptable salt thereof, or the pharmaceutical composition thereof disclosed herein for use in treating or preventing a disease responsive to TLR8 agonism.

In some embodiments of the present application, the disease responsive to TLR8 agonism is viral infection.

In some embodiments of the present application, the viral infection is hepatitis B virus (HBV) infection.

TECHNICAL EFFECTS

The compound disclosed herein has significant agonistic activity for TLR8. The compound disclosed herein exhibits desirable agonistic activity and specific selectivity for TLR8. The compound disclosed herein exhibits desirable activity for inducing TLR8 pathway specific cytokines (IL-12p40, IFN-γ). Pharmacokinetic study in mice shows that the compound disclosed herein has moderate oral bioavailability and drug exposure, and thus oral administration is feasible. TLR8 agonist is an immunomodulator, and its excessive exposure may result in immune overactivation of the body, leading to unpredictable side effects.

DEFINITIONS AND DESCRIPTION

Unless otherwise stated, the following terms and phrases used herein are intended to have the following meanings A particular term or phrase, unless otherwise specifically defined, should not be considered as uncertain or unclear, but construed according to its common meaning. When referring to a trade name, it is intended to refer to its corresponding commercial product or its active ingredient.

The term "pharmaceutically acceptable" is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

The term "pharmaceutically acceptable salt" refers to a salt of the compound disclosed herein, which is prepared from the compound having particular substituents disclosed herein and a relatively nontoxic acid or base. When the compound disclosed herein contains a relatively acidic functional group, a base addition salt can be obtained by contacting the neutral form of such a compound with a sufficient amount of a base in a pure solution or a suitable inert solvent. When the compound disclosed herein contains a relatively basic functional group, an acid addition salt can be obtained by contacting the neutral form of such a compound with a sufficient amount of an acid in a pure solution or a suitable inert solvent. Examples of pharmaceutically acceptable acid addition salt include inorganic acid salts or organic acid salts.

The pharmaceutically acceptable salts disclosed herein can be synthesized from a parent compound having an acidic or basic group by conventional chemical methods. In general, such a salt can be prepared by reacting the compounds in free acid or base form with a stoichiometric amount of an appropriate base or acid in water or an organic solvent or a mixture of the two.

The terms "optional" or "optionally" means that the subsequently described event or circumstance may, but not necessarily, occur. The description includes instances where the event or circumstance occurs and instances where it does not. For example, if an ethyl is optionally substituted by halogen, it means that the ethyl may be unsubstituted ($CH_2CH_3$), monosubstituted (for example, $CH_2CH_2F$), polysubstituted (for example, $CHFCH_2F$, $CH_2CHF_2$ and the like) or fully substituted ($CF_2CF_3$). It will be understood by those skilled in the art that for any groups comprising one or more substituents, any substitutions or substituting patterns which may not exist or cannot be synthesized spatially are not introduced. It will be understood by those skilled in the art that when a group is substituted by multiple substituents, the number of the substituents may be 2, 3, 4, 5 or more, up to all the sites where substitution can occur being substituted. For example, when ethyl is substituted by multiple F atoms, the number of the F atoms may be 2, 3, 4 or 5.

"$C_{m-n}$" used herein means that the portion has an integer number of carbon atoms in the given range. For example, "$C_{1-6}$" means that the group may have 1 carbon atom, 2 carbon atoms, 3 carbon atoms, 4 carbon atoms, 5 carbon atoms or 6 carbon atoms.

The compounds disclosed herein may have a specific geometric or stereoisomeric form. All such compounds are contemplated herein, including cis and trans isomers, (−)- and (+)-enantiomers, (R)- and (S)-enantiomers, diastereoisomers, (D)-isomers, (L)-isomers, and racemic mixtures and other mixtures thereof, such as an enantiomer or diastereoisomer enriched mixture, all of which are encompassed within the scope of the present application. Substituents such as alkyl may have an additional asymmetric carbon atom. All these isomers and mixtures thereof are encompassed within the scope of the present application.

Unless otherwise stated, the term "enantiomer" or "optical isomer" refers to stereoisomers that are mirror images of each other.

Unless otherwise stated, the term "cis-trans isomer" or "geometric isomer" results from the inability of a single bond of a ring carbon atom or a double bond to rotate freely.

Unless otherwise stated, the term "diastereoisomer" refers to stereoisomers in which molecules each have two or more chiral centers and are not mirror images of each other.

Unless otherwise stated, "(D)" or "(+)" stands for dextrorotation, "(L)" or "(−)" stands for levorotation, and "(DL)" or "(±)" stands for racemization.

Unless otherwise stated, the absolute configuration of a stereogenic center is represented by a wedged solid bond ( ◂▸ ) and a wedged dashed bond ( ⋯ ), and the relative configuration of a stereogenic center is represented by a straight solid bond ( ◂▸ ) and a straight dashed bond ( ⋯ ). A wavy line ( ∿ ) represents a wedged solid bond ( ◂▸ ) or a wedged dashed bond ( ⋯ ), or a wavy line ( ∿ ) represents a straight solid bond ( ◂▸ ) and a straight dashed bond ( ⋯ ).

The compounds disclosed herein may be present in particular form. Unless otherwise stated, the term "tautomer" or "tautomeric form" means that different functional isomers are in dynamic equilibrium at room temperature and can be rapidly converted into each other. If tautomers are possible (e.g., in solution), the chemical equilibrium of the tautomers can be achieved. For example, a proton tautomer, also known as a prototropic tautomer, includes the interconversion by proton transfer, such as keto-enol isomerization and imine-enamine isomerization. A valence isomer includes the interconversion by recombination of some bonding electrons. A specific example of the keto-enol tautomerization is the interconversion between tautomers pentane-2,4-dione and 4-hydroxypent-3-en-2-one.

The term "isomer" described herein includes stereoisomers, cis-trans isomers, and tautomers.

Unless otherwise stated, the term "enriched with one isomer", "isomer enriched", "enriched with one enantiomer", or "enantiomer enriched" means that the content of one of the isomers or enantiomers is less than 100% and more than or equal to 60%, 70%, 80%, 90%, 95%, 96%, 97%, 98%, 99%, 99.5%, 99.6%, 99.7%, 99.8%, or 99.9%.

Unless otherwise stated, the term "isomeric excess" or "enantiomeric excess" refers to the difference between the relative percentages of two isomers or enantiomers. For example, if the content of one isomer or enantiomer is 90% and the content of the other isomer or enantiomer is 10%, the isomeric or enantiomeric excess (ee value) is 80%.

Optically active (R)- and (S)-isomers, or D and L isomers can be prepared by chiral synthesis or chiral reagents or other conventional techniques. If one kind of enantiomer of certain compound disclosed herein is to be obtained, the desired pure enantiomer can be prepared by asymmetric synthesis or derivatization using a chiral auxiliary, wherein the resulting diastereoisomeric mixture is separated and the auxiliary group is cleaved. Alternatively, when the molecule contains a basic functional group (such as amino) or an acidic functional group (such as carboxyl), the compound reacts with an appropriate optically active acid or base to form a salt of the diastereoisomer, which is then subjected to diastereoisomeric resolution through conventional methods in the art to get the pure enantiomer. Furthermore, the enantiomer and the diastereoisomer are generally isolated through chromatography using a chiral stationary phase, optionally in combination with chemical derivatization (e.g., carbamate generated from amine).

The compound disclosed herein may contain an unnatural proportion of atomic isotope at one or more of the atoms that constitute the compound. For example, the compound may be labeled with a radioisotope, such as tritium ($^3H$), iodine-125 ($^{125}I$), or C-14 ($^{14}C$). For another example, hydrogen can be substituted by deuterium to form a deuterated drug, and the bond formed by deuterium and carbon is firmer than that formed by common hydrogen and carbon. Compared with an un-deuterated drug, the deuterated drug has the advantages of reduced toxic side effect, increased stability, enhanced efficacy, prolonged biological half-life and the like. All isotopic variations of the compound described herein, whether radioactive or not, are encompassed within the scope of the present application. "Optional" or "optionally" means that the subsequently described event or circumstance may, but not necessarily, occur, and the description includes instances where the event or circumstance occurs and instances where it does not.

The term "substituted" means that one or more hydrogen atoms on a specific atom are substituted by substituent(s) which may include deuterium and hydrogen variants, as long as the valence of the specific atom is normal and the substituted compound is stable. When the substituent is an oxygen (i.e., =O), it means that two hydrogen atoms are substituted. Substitution by oxygen does not occur on aromatic groups. The term "optionally substituted" means that an atom can be substituted by a substituent or not. Unless otherwise specified, the type and number of the substituent may be arbitrary as long as being chemically achievable.

When any variable (e.g., R) occurs more than once in the constitution or structure of a compound, the definition of the variable in each case is independent. Thus, for example, if a group is substituted by 0-2 R, the group can be optionally substituted by two R at most, and the definition of R in each case is independent. Furthermore, a combination of a substituent and/or a variant thereof is permissible only if the combination can result in a stable compound.

Unless otherwise specified, the term "$C_{1-6}$ alkyl" refers to a linear or branched saturated hydrocarbon group containing 1 to 6 carbon atoms. The $C_{1-6}$ alkyl includes $C_{1-4}$, $C_{1-3}$, $C_{1-2}$, $C_{2-6}$, $C_{2-4}$, $C_6$, $C_5$ alkyl and the like; it may be monovalent (e.g., methyl), divalent (e.g., methylene) or polyvalent (e.g., methenyl). Examples of $C_{1-6}$ alkyl include, but are not limited to, methyl (Me), ethyl (Et), propyl (including n-propyl and isopropyl), butyl (including n-butyl, isobutyl, s-butyl, and t-butyl), pentyl (including n-pentyl, isopentyl, and neopentyl), hexyl, and the like.

Unless otherwise specified, "$C_{3-6}$ cycloalkyl" refers to a saturated cyclic hydrocarbon group consisting of 3 to 6 carbon atoms, including monocyclic and bicyclic ring systems. The $C_{3-6}$ cycloalkyl includes $C_{3-5}$ cycloalkyl, $C_{4-5}$ cycloalkyl, $C_{5-6}$ cycloalkyl and the like, and may be monovalent, divalent or polyvalent. Examples of $C_{3-6}$ cycloalkyl include, but are not limited to, cyclopropyl, cyclobutyl, cyclopentyl, cyclohexyl and the like.

The term "pharmaceutical composition" refers to a mixture consisting of one or more of the compounds or pharmaceutically acceptable salts thereof disclosed herein and a pharmaceutically acceptable excipient. The pharmaceutical composition is intended to facilitate the administration of the compound to an organic entity.

The term "pharmaceutically acceptable excipients" refers to those which do not have a significant irritating effect on an organic entity and do not impair the biological activity and properties of the active compound. Suitable excipients are well known to those skilled in the art, such as carbohydrate, wax, water-soluble and/or water-swellable polymers, hydrophilic or hydrophobic material, gelatin, oil, solvent, and water.

The term "treating" means administering the compound or formulation described herein to ameliorate or eliminate a disease or one or more symptoms associated with the disease, and includes:

(i) inhibiting a disease or disease state, i.e., arresting its development; and (ii) alleviating a disease or disease state, i.e., causing its regression.

The term "therapeutically effective amount" refers to an amount of the compound disclosed herein for (i) treating a specific disease, condition, or disorder, or (ii) alleviating, ameliorating, or eliminating one or more symptoms of a specific disease, condition, or disorder. The amount of the compound disclosed herein composing the "therapeutically effective amount" varies dependently on the compound, the disease state and its severity, the administration regimen, and the age of the mammal to be treated, but can be determined routinely by those skilled in the art in accordance with their knowledge and the present disclosure.

The term "preventing" means administering the compound or formulation described herein to prevent a disease or one or more symptoms associated with the disease, and includes: preventing the occurrence of the disease or disease state in a mammal, particularly when such a mammal is predisposed to the disease state but has not yet been diagnosed as having it.

The following abbreviations are used in this application:

| | |
|---|---|
| Pd/C | Pd/C catalyst, containing 10 w % palladium |
| DCM | Dichloromethane |
| THF | Tetrahydrofuran |
| Boc | Tert-butyloxycarbonyl, an amine protecting group |
| Cbz | Benzyloxycarbonyl, an amine protecting group |
| DMF | N,N-dimethylformamide |
| TFA | Trifluoroacetic acid |
| PE | Petroleum ether |
| DMSO | Dimethyl sulfoxide |
| EtOH | Ethanol |
| MeOH | Methanol |
| HOAc | Acetic acid |
| Trt | Triphenylmethyl |
| CbzCl | Benzyl chloroformate |
| DIPEA | Diisopropylethylamine |
| $SiO_2$ | 100-200 mesh silica gel powder, for column chromatography |
| psi | Pound force/square inch, unit of pressure |
| p-HPLC | Preparative high performance liquid chromatography, for the purification of compounds |

The solvents used herein are commercially available and do not require further purification. The reaction is generally performed in an anhydrous solvent under nitrogen atmosphere. Proton nuclear magnetic resonance data are recorded on a Bruker Avance III 400 (400 MHz) spectrometer and chemical shifts reported as ppm downfield from tetramethylsilane. Mass spectra are determined on an Agilent 1200 series plus 6110 (& 1956A). LC/MS or Shimadzu MS includes a DAD: SPD-M20A (LC) and Shimadzu Micromass 2020 detector. The mass spectrometer is equipped with an electrospray ionsource (ESI) operated in either positive or negative mode.

The Shimadzu LC20AB system equipped with a Shimadzu SIL-20A automatic sampler and a Shimadzu DAD: SPD-M20A detector was used for analysis of high performance liquid chromatography with an Xtimate C18 (3 m filler, specification: 2.1×300 mm) chromatographic column.

SPECIFIC EMBODIMENTS

The present application is described in detail below by way of examples. However, this is by no means disadvantageously limiting the scope of the present application. Although the present application has been described in detail herein and specific examples have also been disclosed, it will be apparent to those skilled in the art that various changes and modifications can be made to the specific embodiments without departing from the spirit and scope of the present application.

Example 1

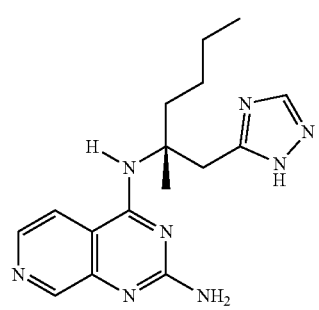

Preparation of intermediate compound 1-10:

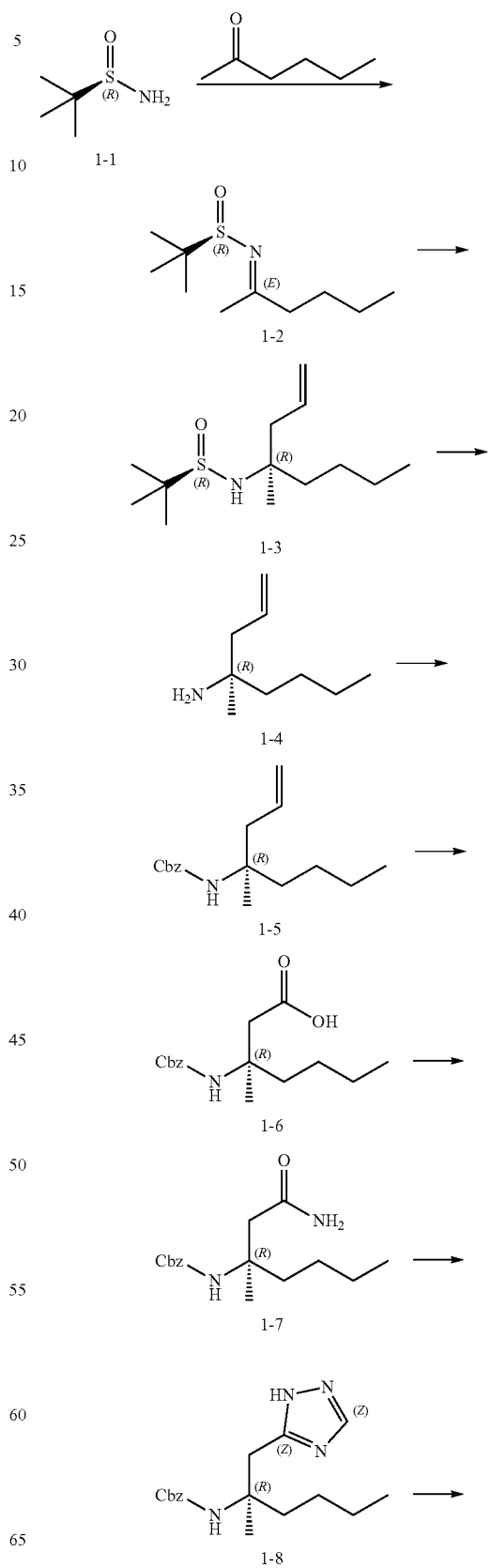

-continued

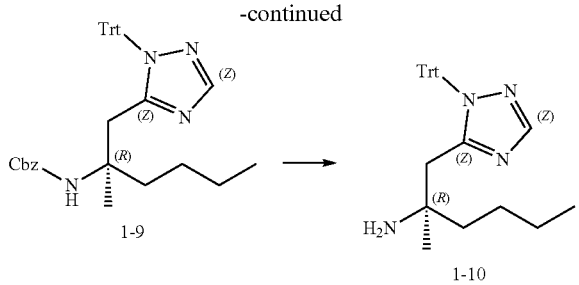

Step A: compound 1-1 (50 g, 412.54 mmol) and tetraethyl titanate (94.10 g, 412.54 mmol, 85.55 mL) were dissolved in THF (500 mL) at 20-30° C., and the solution was added with 2-hexanone (41.32 g, 412.54 mmol, 51.01 mL). The reaction mixture was warmed to 65° C. and stirred for 48 hours, and the resulting reaction mixture was used directly in the next step.

Step B: the reaction mixture in step A was cooled to room temperature, supplemented with THF (1000 mL), then added with allyl bromide (196.33 g, 1.62 mol), and slowly added with zinc powder (53.06 g, 811.43 mmol) in portions. The reaction mixture was stirred at 20-30° C. for 12 hours under nitrogen atmosphere. The reaction mixture was filtered through diatomite, and the filtrate was added with saturated brine (100 mL), stirred, and filtered through diatomite. The resulting filtrate was dried with a rotary evaporator. The residue was dissolved in ethyl acetate (100 mL). The separated organic phase was washed with saturated brine (300 mL×1), dried over anhydrous sodium sulfate, filtered and concentrated under reduced pressure to give a crude product. The crude product was purified by column chromatography (SiO$_2$, PE/EtOAc=15/1 to 5/1) to give compound 1-3. $^1$H NMR (400 MHz, CDCl$_3$) δ 5.96-5.75 (m, 1H), 5.23-5.08 (m, 2H), 3.20 (s, 1H), 2.39-2.20 (m, 2H), 1.74 (br s, 1H), 1.56-1.42 (m, 2H), 1.40-1.15 (m, 14H), 0.96-0.86 (m, 3H).

Step C: compound 1-3 (15 g, 61.12 mmol) was dissolved in methanol (150 mL), and the solution was cooled to 0° C. and slowly added with dioxane solution of hydrochloric acid (4 M, 91.68 mL) at 0-20° C. The reaction mixture was stirred at 25° C. for 2 hours. The reaction mixture was directly concentrated under reduced pressure to give compound 1-4.

Step D: compound 1-4 (hydrochloride, 13 g, 73.15 mmol) and sodium bicarbonate (55.31 g, 658.36 mmol) were dissolved in dioxane (90 mL) and H$_2$O (60 mL), and the solution was cooled to 0° C. and then slowly added with CbzCl (74.87 g, 438.91 mmol, 62.40 mL) dropwise. The reaction mixture was warmed to 20-30° C., stirred for 2 hours, and extracted with ethyl acetate (100 mL×2). The organic phases were combined, washed with saturated brine (150 mL×1), dried over anhydrous sodium sulfate, filtered and concentrated under reduced pressure to give a crude product. The crude product was purified by column chromatography (SiO$_2$, PE/EtOAc=1/0 to 100/1) to give compound 1-5. $^1$H NMR (400 MHz, CDCl$_3$) δ 7.30-7.26 (m, 5H), 5.76-5.62 (m, 1H), 5.08-4.91 (m, 4H), 2.47-2.34 (m, 1H), 2.32-2.20 (m, 1H), 1.72-1.57 (m, 1H), 1.50-1.42 (m, 1H), 1.30-1.10 (m, 7H), 0.76-0.76 (m, 1H), 0.76-0.76 (m, 1H), 0.82 (t, J=7.0 Hz, 2H).

Step E: compound 1-5 (20.8 g, 75.53 mmol) was dissolved in acetonitrile (100 mL), H$_2$O (150 mL) and carbon tetrachloride (100 mL), and the solution was cooled to 0° C. and slowly added with sodium periodate (64.62 g, 302.12 mmol), followed by the addition of ruthenium trichloride trihydrate (394.99 mg, 1.51 mmol) The reaction mixture was warmed to 25° C. and stirred for 2 hours. The reaction mixture was filtered through diatomite and extracted with DCM (200 mL×1). The organic phase was washed with saturated aqueous sodium sulfite solution (200 mL×1) and saturated brine (200 mL×1) sequentially, dried over anhydrous sodium sulfate, filtered and concentrated under reduced pressure to give crude compound 1-6, which was used directly in the next step. $^1$H NMR (400 MHz, CDCl$_3$) δ 7.40-7.35 (m, 5H), 5.19 (s, 1H), 5.08 (s, 2H), 2.89 (br d, J=14.5 Hz, 1H), 2.69 (br d, J=14.4 Hz, 1H), 1.90-1.77 (m, 1H), 1.74-1.62 (m, 1H), 1.43-1.20 (m, 7H), 0.90 (t, J=6.9 Hz, 3H).

Step F: compound 1-6 (20 g, 68.18 mmol) and triethylamine (10.35 g, 102.26 mmol, 14.23 mL) were dissolved in THF (250 mL), and the solution was added with isobutyl chloroformate (9.78 g, 71.59 mmol, 9.40 mL) dropwise at −10° C. under nitrogen atmosphere. The reaction mixture was stirred for 30 minutes at −10-0° C. The reaction mixture was slowly added with ammonia water (63.70 g, 454.41 mmol, 70 mL, 25%) and stirred at 0-5° C. for 30 minutes. The reaction mixture was concentrated under reduced pressure and extracted with ethyl acetate (200 mL×1). The organic phase was washed with saturated brine (100 mL×2), dried over anhydrous sodium sulfate, filtered and concentrated under reduced pressure to give a crude product. The crude product was purified by column chromatography (SiO$_2$, PE/EtOAc=10/1 to 1/1) to give compound 1-7. $^1$H NMR (400 MHz, CDCl$_3$) δ 7.41-7.28 (m, 5H), 5.62 (br s, 1H), 5.30-5.12 (m, 2H), 5.11-5.01 (m, 2H), 2.76 (d, J=13.2 Hz, 1H), 2.44 (d, J=13.3 Hz, 1H), 1.85-1.74 (m, 1H), 1.73-1.62 (m, 3H), 1.39-1.29 (m, 5H), 0.90 (t, J=7.0 Hz, 3H). LCMS (ESI) m/z: 293.3 [M+H]$^+$.

Step G: compound 1-7 (15.34 g, 52.47 mmol) and N,N-dimethylformamide dimethyl acetal (134.55 g, 1.13 mol, 150 mL) were stirred at 120° C. for 2 hours, concentrated under reduced pressure, and dissolved in acetic acid (250 mL), and the solution was slowly added with hydrazine hydrate (25.75 g, 504.09 mmol, 25 mL, 98%). The reaction mixture was stirred at 90° C. for 2 hours under nitrogen atmosphere. The reaction mixture was concentrated under reduced pressure, added with H$_2$O (400 mL), and extracted with DCM (200 mL×2). The organic phases were combined, washed with saturated brine (200 mL×2), dried over anhydrous sodium sulfate, filtered and concentrated under reduced pressure to give crude compound 1-8. $^1$H NMR (400 MHz, CDCl$_3$) δ 7.95 (s, 1H), 7.43-7.29 (m, 5H), 5.08 (s, 2H), 4.90 (br s, 1H), 3.42 (br d, J=13.9 Hz, 1H), 3.12 (d, J=14.3 Hz, 1H), 1.87-1.77 (m, 1H), 1.68-1.58 (m, 1H), 1.41-1.17 (m, 7H), 0.90 (br t, J=6.5 Hz, 3H). LCMS (ESI) m/z: 317.2 [M+H]$^+$.

Step H: compound 1-8 (15.20 g, 48.04 mmol) and DIPEA (12.42 g, 96.08 mmol, 16.74 mL) were dissolved in DCM (160 mL), and the solution was slowly added with triphenylchloromethane (20.09 g, 72.06 mmol) The reaction mixture was stirred at 25° C. for 2 hours. The reaction mixture was added with H$_2$O (100 mL), added with 2 N diluted hydrochloric acid to adjust the pH (7-8), and extracted with DCM (100 mL×1). The organic phase was washed with saturated brine (100 mL×2), dried over anhydrous sodium sulfate, filtered and concentrated under reduced pressure to give a crude product. The crude product was purified by column chromatography (SiO$_2$, PE/EtOAc=20/1 to 5/1) to give compound 1-9. $^1$H NMR (400 MHz, CDCl$_3$) δ 7.89 (s, 1H), 7.37-7.27 (m, 14H), 7.18-7.07 (m, 6H), 5.72 (br s, 1H), 5.16-4.93 (m, 2H), 3.07

(d, J=14.2 Hz, 1H), 2.90 (d, J=14.2 Hz, 1H), 1.80-1.61 (m, 4H), 1.33 (s, 3H), 0.90-0.84 (m, 3H). LCMS (ESI) m/z: 559.3 [M+H]$^+$.

Step I: compound 1-9 (12.75 g, 22.82 mmol) was dissolved in isopropanol (300 mL), and the solution was added with Pd/C (6 g) under nitrogen atmosphere. The suspension was degassed under vacuum and purged with hydrogen three times, and stirred at 25° C. for 16 hours under hydrogen atmosphere (15 psi). The reaction mixture was filtered through diatomite and washed with DCM (300 mL), and the filtrate was concentrated under reduced pressure to give compound 1-10. $^1$H NMR (400 MHz, CDCl$_3$) δ 7.91 (s, 1H), 7.37-7.28 (m, 9H), 7.17-7.11 (m, 6H), 2.87 (s, 2H), 1.45-1.24 (m, 6H), 1.12 (s, 3H), 0.92-0.84 (m, 3H). LCMS (ESI) m/z: 425.2 [M+H]$^+$.

Synthesis of Example 1

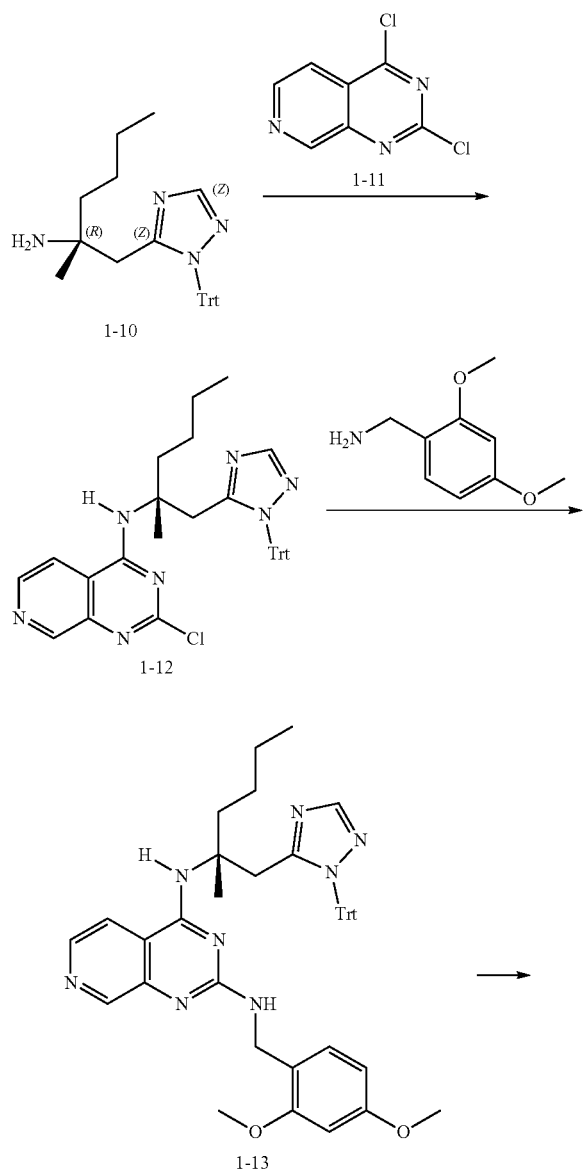

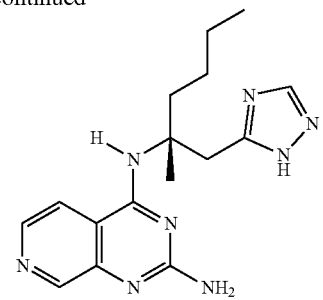

Hydrochloride of Example 1

Step A: compound 1-10 (1.91 g, 4.50 mmol) and compound 1-11 (900 mg, 4.50 mmol) were dissolved in THF (9 mL), and the solution was added with DIPEA (9.00 mmol, 1.57 mL). The reaction mixture was stirred at 70° C. for 3 hours under nitrogen atmosphere. The reaction mixture was concentrated under reduced pressure to give crude compound 1-12. LCMS (ESI) m/z: 588.42 [M+H]$^+$.

Step B: crude compound 1-12 (3.60 g, 6.12 mmol) and 2,4-dimethoxybenzylamine (3.01 mg, 18.00 mmol, 2.71 mL) were dissolved in 1,4-dioxane (30 mL), and the solution was added with DIPEA (8.99 mmol, 1.57 mL) under nitrogen atmosphere. The reaction mixture was stirred at 100° C. for 12 hours. The reaction mixture was added with water (20 mL) and ethyl acetate (50 mL) for liquid separation. The organic phase was washed with saturated brine (20 mL), dried over anhydrous sodium sulfate, filtered and concentrated under reduced pressure to give a crude product. The crude product was purified by silica gel column chromatography (SiO$_2$, DCM/MeOH=100/1 to 15/1) to give compound 1-13. LCMS (ESI) m/z: 719.7 [M+H]$^+$.

Step C: compound 1-13 (2.00 g, 2.78 mmol) and triethylsilane (970.50 mg, 8.35 mmol, 1.33 mL) were dissolved in TFA (41.81 mL), and the solution was stirred at 28° C. for 12 hours. The reaction mixture was directly concentrated under reduced pressure and purified by p-HPLC (column: Phenomenex lung. C18 250×50 mm×10 µm; fluidity: [water (0.05% HCl)-acetonitrile]; acetonitrile %: 10%-40%, 28 min, 50% min) to give the hydrochloride of Example 1. $^1$H NMR (400 MHz, CD$_3$OD) δ 9.15 (s, 1H), 8.90 (s, 1H), 8.59 (d, J=5.6 Hz, 1H), 8.26 (d, J=5.5 Hz, 1H), 4.11 (d, J=14.8 Hz, 1H), 3.53 (d, J=14.9 Hz, 1H), 2.60 (dt, J=4.1, 12.8 Hz, 1H), 1.79 (dt, J=4.2, 12.8 Hz, 1H), 1.58 (s, 3H), 1.52-1.19 (m, 4H), 0.92 (t, J=7.2 Hz, 3H). LCMS (ESI) m/z: 327.1 [M+H]$^+$.

Experimental Example 1: Screening for In Vitro Receptor Binding Activity of Human Toll-Like Receptor 7 (TLR7) and Human Toll-Like Receptor 8 (TLR8)

The HEK-Blue™ hTLR7 (catalog No. hkb-htlr7) and HEK-Blue™ hTLR8 (catalog No. hkb-ht1r8) cell lines used in this experiment were purchased from InvivoGen. The two cell lines were constructed by a human embryonic kidney 293 cell line stably co-transfecting hTLR7 or hTLR8 and inducing expression of Secreted Alkaline Phosphatase (SEAP) reporter gene, wherein SEAP reporter gene was regulated by an IFN-β promoter. The promoter was fused with NF-κB and AP-1 binding sites. hTLR7 or hTLR8 agonist can activate NF-κB and AP-1 and induce the expression and secretion of SEAP. The agonistic activity of compound for hTLR7 and hTLR8 receptors was identified by measuring the expression level of SEAP using QUANTI-Blue™ reagent.

The experimental procedures are as follows:
1. Compound was added to a cell plate in a 3-fold gradient, with the final concentrations being 5000 nM, 1667 nM, 556 nM, 185 nM, 62 nM, 21 nM, 6.9 nM, 2.3 nM, 0.76 nM and 0.25 nM respectively, and two duplicate wells were provided for each concentration. 1 μL of DMSO was added to each negative control well.
2. The cells cultured in a T150 flask were taken out from a $CO_2$ incubator, and the cell culture supernatant was discarded. The resulting cells were washed once with Dulbecco's phosphate buffered saline (DPBS). The flask was added with about 10 mL of the culture medium, and tapped to detach the cells. The resulting cell mass was gently pipetted evenly. The cells were counted and the cell suspension was adjusted to 500,000 cells/mL with the culture medium. Then 100 μL of diluted cells (50,000 cells/well) were added to each well of a 96-well plate containing the compound.
3. The compound and cells were incubated in an incubator at 37° C., 5% $CO_2$ for 24 hours.
4. Activity assay on the compound: 20 μL of the induced cell supernatant from each well was added to a cell culture plate containing 180 μL of QUANTI-Blue™ reagent, and after incubation at 37° C. for 1 hour, the optical density absorbance at 650 nm ($OD_{650}$) was assayed for each well using a multi-functional microplate reader.
5. Activity assay on the cells: luciferase signal (RLU) was detected using a multi-functional microplate reader as per the process described in the instructions of ATPlite 1 Step.
6. Data analysis: compound activity: $OD_{650}$ values were analyzed using a GraphPad Prism software and the dose-response curves of the compound were fitted to calculate $EC_{50}$ values (half maximal effect concentration) for the compound.

Experimental Results: the results are shown in Table 1.

TABLE 1

| Test compound | Human TLR8 $EC_{50}$ (μM) | Human TLR7 $EC_{50}$ (μM) |
|---|---|---|
| Hydrochloride of Example 1 | 0.003 | 33.33 |

Conclusion: the compound disclosed herein exhibits desirable TLR8 agonist activity and, in terms of TLR8 and TLR7, has specific selectivity for TLR8.

Experimental Example 2: Experimental Procedure for Peripheral Blood Mononuclear Cell TLR8 is a receptor for the innate immune system to sense exogenous pathogens, and can recognize exogenous viral single-stranded RNA and cause the release of a series of cytokines such as TNF-α, IL-12, IFN-γ to elicit an antiviral immune response; TLR7 is another receptor for the innate immune system to sense exogenous pathogens and, when activated, produces primarily such antiviral cytokines as IFN-α. In this experiment, a potential compound of TLR8 agonist was used to stimulate human peripheral blood mononuclear cells (hPBMCs), and the levels of TNF-α, IL-12p40, IFN-γ and IFN-α above were measured to reflect the activation of the compound on TLR8 receptor and its selectivity for TLR8/TLR7.

The experimental procedures are as follows:
1. Fresh blood of healthy volunteers was collected, and anticoagulated with an EDTA-K2 anticoagulation tube (catalog No. BD-8516542);
2. hPBMC cells in the middle cloud-like layer were separated after Ficoll density gradient centrifugation, and washed twice with RPMI1640 (source: Gibco, catalog No. 224400-089) containing 10% serum, and the culture medium was resuspended to 10 mL. After the cells were counted with Vi-cell cell counter, the concentration of cell suspension was adjusted to $2\times10^6$/mL;
3. The compound was dissolved in DMSO to 100 mM, and diluted to 50 mM and 2 mM with DMSO, which were served as initial concentrations. Then the solutions were each diluted sequentially in a 3-fold gradient (sample at a previous concentration (5 μL)+DMSO (10 μL)) to obtain 8 gradients. The resulting solutions were respectively subjected to 500-fold dilution with the culture medium to prepare the working solutions of the compound;
4. 100 μL of hPBMC suspension and 100 μL of compound working solution were added to each well of a U-bottom 96-well plate, with the final concentrations being 2000 nM, 666.7 nM, 222.2 nM, 74.1 nM, 24.7 nM, 8.2 nM, 2.7 nM and 0.9 nM respectively, and incubated for 24 hours. Then the supernatants were collected and cryopreserved at −20° C. for the detection of TNF-α, IFN-γ and IL-12p40 cytokines. The other group of compound samples, with the final concentrations being 50 μM, 16.7 μM, 5.6 μM, 1.9 μM, 0.6 μM, 0.2 μM, 0.1 μM and 0.02 μM respectively, were incubated for 24 hours. The supernatants were collected and cryopreserved at −20° C. for the detection of IFN-α cytokines;
5. IL-12p40, TNF-α and IFN-γ in the supernatant were detected by flow cytometric bead array (CBA); IFN-α in the cell supernatant was detected by enzyme-linked immuno sorbent assay (ELISA).
6. Data analysis: compound activity: $EC_{50}$ values (half maximal effect concentration) were analyzed using a GraphPad Prism software and the dose-response curves of the compound were fitted to calculate $EC_{50}$ values for the compound.

Experimental results: the results are shown in Table 2.

TABLE 2

| Test compound | IL-12p40 $EC_{50}$ (nM) | IFN-γ $EC_{50}$ (nM) | TNF-α $EC_{50}$ (nM) | IFN-α $EC_{50}$ (nM) |
|---|---|---|---|---|
| Hydrochloride of Example 1 | 26 | 29 | 105 | 2800 |

Conclusion: the compound disclosed herein has desirable induction activity for TLR8 pathway specific cytokines IL-12p40, TNF-α and IFN-γ, and relatively low induction activity for TLR7 pathway specific cytokine IFN-α, showing desirably specific selectivity for TLR8 pathway activation.

Experimental Example 3: Pharmacokinetic Study in Mice

This experiment was intended to evaluate the pharmacokinetic behavior of the compound after a single intravenous injection or intragastric administration in mice. Intravenous injection: the test compound was prepared into a 0.5 mg/mL clear solution, with the vehicle being 5% DMSO/5% polyethylene glycol-15 hydroxystearate/90% water; intragastric administration: the test compound was prepared into a 2 mg/mL suspension, with the vehicle being 0.5% sodium carboxymethylcellulose/0.2% tween 80/99.3% water.

The concentration of the test compound in plasma was determined by high performance liquid chromatography-tandem mass spectrometry (LC-MS/MS). The retention times of the compound and internal standard, chromatogram acquisitions and integrals of chromatograms were processed using the software Analyst (Applied Biosystems), and the data statistics were processed using the software Watson LIMS (Thermo Fisher Scientific) or Analyst (Applied Biosystems).

The plasma concentrations were processed using a non-compartmental model of WinNonlin™ Version 6.3 (Pharsight, Mountain View, CA), a pharmacokinetic software, and the pharmacokinetic parameters were calculated using a linear-log trapezoidal method.

The related pharmacokinetic parameters in the mice at 1 mg/Kg intravenous injection and 5 mg/Kg oral intragastric administration of the hydrochloride of Example 1 are shown in Table 3 below.

TABLE 3

Related pharmacokinetic parameters in mice

| | | |
|---|---|---|
| Intravenous injection (1 mg/Kg) | Cl (mL/min/kg) | 90.2 |
| | Vdss (L/kg) | 1.75 |
| | $t_{1/2}$ (hour) | 0.25 |
| | $AUC_{0\text{-}last}$ (nM · hr) | 450 |
| Oral intragastric administration (5 mg/Kg) | $T_{max}$ (hour) | 0.5 |
| | $C_{max}$ (nM) | 421 |
| | $AUC_{0\text{-}last}$ (nM · hr) | 624 |
| | Bioavailability (F %) | 27.7 |

The invention claimed is:

1. A compound of formula (I), an isomer thereof or a pharmaceutically acceptable salt thereof,

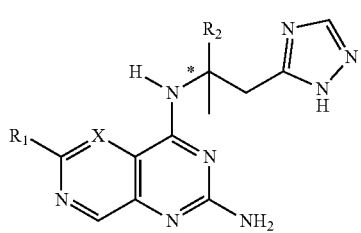

wherein,
the carbon atom with "*" is optionally a chiral carbon atom;
X is selected from the group consisting of N and CH;
$R_1$ is selected from the group consisting of H, F, Cl, Br, I, CN, $C_{1-6}$ alkyl, $C_{3-6}$ cycloalkyl, —N($R_a$)($R_b$) and —O($R_c$), the $C_{1-6}$ alkyl and $C_{3-6}$ cycloalkyl being optionally substituted with 1, 2 or 3 $R_d$;
$R_2$ is $C_{1-6}$ alkyl, the $C_{1-6}$ alkyl being optionally substituted with 1, 2 or 3 $R_e$;
$R_a$, $R_b$, $R_c$, $R_d$ and $R_e$ are each independently selected from the group consisting of H, F, Cl, Br, I, OH, CN, $NH_2$, $CH_3$,

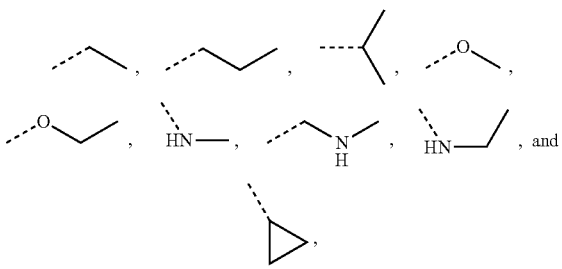

the $CH_3$,

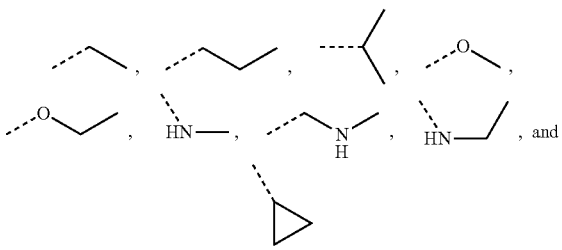

being optionally substituted with 1, 2 or 3 R; and
each R is independently selected from the group consisting of F, Cl, Br, I, OH, CN, $NH_2$, $CH_3$,

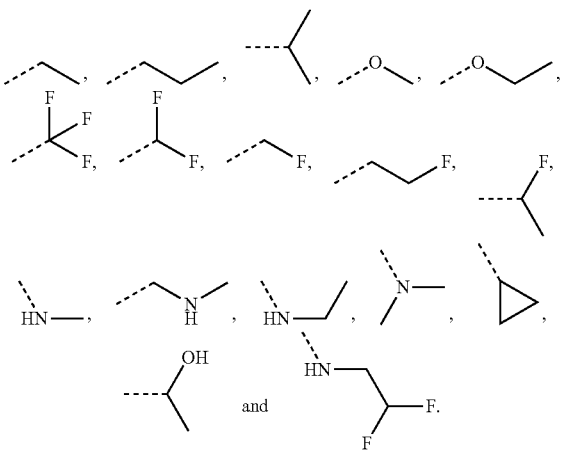

2. The compound, the isomer thereof or the pharmaceutically acceptable salt thereof according to claim 1, wherein $R_a$, $R_b$, $R_c$, $R_d$ and $R_e$ are each independently selected from the group consisting of H, F, Cl, Br, I, OH, CN, $NH_2$, $CH_3$,

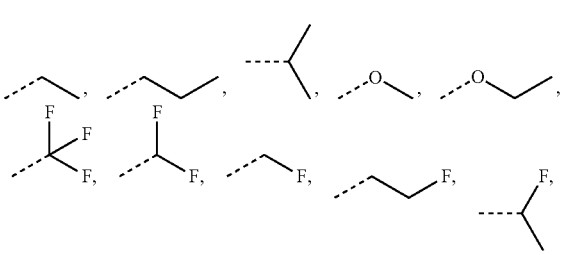

3. The compound, the isomer thereof or the pharmaceutically acceptable salt thereof according to claim 1, wherein $R_1$ is selected from the group consisting of H, F, Cl, Br, I, CN, $CH_3$,

[structures], cyclopentyl, cyclobutyl,

[structures], $NH_2$,

[structures], and the $CH_3$,

[structures], cyclopentyl and cyclobutyl being optionally substituted with 1, 2 or 3 $R_d$.

4. The compound, the isomer thereof or the pharmaceutically acceptable salt thereof according to claim 1, wherein $R_1$ is selected from the group consisting of H, F, Cl, Br, I, $CH_3$ and

[structure].

5. The compound, the isomer thereof or the pharmaceutically acceptable salt thereof according to claim 1, wherein $R_2$ is selected from the group consisting of

[structures], and the

[structures], and being optionally substituted with 1, 2 or 3 $R_e$.

6. The compound, the isomer thereof or the pharmaceutically acceptable salt thereof according to claim 5, wherein $R_2$ is

[structure].

7. A compound of the formula below, an isomer thereof or a pharmaceutically acceptable salt thereof,

[structure]

8. The compound, the isomer thereof or the pharmaceutically acceptable salt thereof according to claim 7, wherein the compound is

[structure]

9. A pharmaceutical composition comprising the compound, the isomer thereof or the pharmaceutically acceptable salt thereof according to claim 1.

10. A method for treating a viral infection, comprising administering to a subject in need of a therapeutically effective amount of the compound, the isomer thereof or the pharmaceutically acceptable salt thereof according to claim 1, wherein the viral infection is a hepatitis B virus infection.

11. A method for treating a viral infection, comprising administering to a subject in need of a therapeutically effective amount of the pharmaceutical composition according to claim 9, wherein the viral infection is a hepatitis B virus infection.

* * * * *